US012403143B2

(12) United States Patent
Morozova et al.

(10) Patent No.: US 12,403,143 B2
(45) Date of Patent: Sep. 2, 2025

(54) PHARMACEUTICAL COMPOSITION FOR TREATING FUNCTIONAL PSYCHIATRIC DISORDERS (71) Applicant: OBSCHESTVO S OGRANICHENNOI OTVETSTVENNOSTYU "VALENTEK", Moscow (RU)

(72) Inventors: Margarita Alekseevna Morozova, Moscow (RU); Allan Gerovich Beniashvili, Moscow (RU); Maksim Eduardovich Zapolsky, Moskovskaya obl. (RU); Vladimir Viktorovich Nesteruk, Moscow (RU)

( * ) Notice: Subject to any disclaimer, the term of this patent is extended or adjusted under 35 U.S.C. 154(b) by 1187 days.

(21) Appl. No.: 16/082,090

(22) PCT Filed: Nov. 15, 2016

(86) PCT No.: PCT/RU2016/000783
§ 371 (c)(1),
(2) Date: Sep. 4, 2018

(87) PCT Pub. No.: WO2017/151006
PCT Pub. Date: Sep. 8, 2017

(65) Prior Publication Data
US 2019/0275059 A1 Sep. 12, 2019

(30) Foreign Application Priority Data
Mar. 4, 2016 (RU) .......................... RU2016107968

(51) Int. Cl.
A61P 25/18 (2006.01)
A61K 31/5513 (2006.01)
A61P 25/24 (2006.01)

(52) U.S. Cl.
CPC .......... *A61K 31/5513* (2013.01); *A61P 25/18* (2018.01); *A61P 25/24* (2018.01)

(58) Field of Classification Search
CPC ........................ A61K 31/5513; A61P 25/18
See application file for complete search history.

(56) References Cited

U.S. PATENT DOCUMENTS

| 5,538,965 A | 7/1996 | Tehim et al. |
| 10,391,101 B2 * | 8/2019 | Zapolski ............... A61K 9/2013 |
| 2011/0172210 A1 * | 7/2011 | Mulligan ............. A61P 25/18 514/220 |
| 2017/0196883 A1 | 7/2017 | Zapolski et al. |

FOREIGN PATENT DOCUMENTS

| DE | 2413610 A1 * | 10/1974 | ........... C07D 491/04 |
| EP | 2 641 907 | 9/2013 | |
| RU | 2 441 867 | 2/2012 | |
| RU | 2 497 819 | 11/2013 | |
| WO | WO 2004/014895 | 2/2004 | |
| WO | WO 2008/021463 | 2/2008 | |
| WO | WO 2013/070107 | 5/2013 | |

OTHER PUBLICATIONS

Wasserman et al. (Probabilistic classification and gambling in patients with schizophrenia receiving medication: comparison of risperidone, olanzapine, clozapine and typical antipsychotics. Psychopharmacology 222, 173-183 (2012). https://doi.org/10.1007/s00213-011-2634-4 (Year: 2012).*
Rotondo et al. ("Clozapine for medication-related pathological gambling in Parkinson disease." Movement Disorder (2010); vol. 25 (Issue 12): pp. 1994-1995). (Year: 2010).*
WO2013070107. English translation. (Year: 2013).*
Alvir et al., "Clozapine-Induced Agranulocytosis—Incidence and Risk Factors in the United States" *The New England Journal of Medicine*, vol. 329, No. 3: 162-167 (Jul. 15, 1993).
Ben-Aryeh et al., "Salivary Flow-Rate and Composition in Schizophrenic Patients on Clozapine: Subjective Reports and Laboratory Data" *Biol Psychiatry*, vol. 39: 946-949 (1996).
Dain et al., "Biotransformation of Clozapine in Humans" *Drug Metabolism and Disposition*, vol. 25, No. 5: 603-609 (1997).
Fisher, "Cholinergic Treatments with Emphasis on M1 Muscarinic Agonists as Potential Disease-Modifying Agents for Alzheimer's Disease" *Neurotherapeutics: The Journal of the American Society for Experimental Neuro Therapeutics*, vol. 5: 433-442 (Jul. 2008).
Guest et al., "Drugs that induce neutropenia/agranulocytosis may target specific components of the stromal cell extracellular matrix" *Medical Hypotheses*, vol. 53, No. 2: 145-151 (1999).
Iverson et al., "Effect of Clozapine on Neutrophil Kinetics in Rabbits" *Chem. Res. Toxicol.*, vol. 23: 1184-1191 (2010).
Kane et al., "Clozapine for the Treatment-Resistant Schizophrenic" *Arch Gen Psychiatry*, vol. 45: 789-796 (Sep. 1988).
Knable et al., "Extrapyramidal side effects with risperidone and haloperidol at comparable D2 receptor occupancy levels" *Psychiatry Research: Neuroimaging*, vol. 75: 91-101 (1997).
Lehman et al., "Practice Guideline for the Treatment of Patients With Schizophrenia" Second Edition, *Am J Psychiatry*, vol. 161: 1-56 (Feb. 2004).
Leucht et al., "Comparative efficacy and tolerability of 15 antipsychotic drugs in schizophrenia: a multiple-treatments meta-analysis" *Lancet*, vol. 382: 951-962 (Sep. 14, 2013).

(Continued)

Primary Examiner — James H Alstrum-Acevedo
Assistant Examiner — Chris E Simmons
(74) Attorney, Agent, or Firm — Nixon & Vanderhye PC (57) ABSTRACT The group of inventions relates to medicine, pharmacology, namely to psychiatry and can be used for effective and safe treatment of mental disorders associated with dysfunction of dopamine and serotonin (5-hydroxytryptamine) neurotransmitter systems. Pharmaceutical compositions containing halogenated clozapine, in an amount effective as selective antagonists of D4 and 5NT2A receptors, and at least one pharmaceutically acceptable carrier, as well as their use and methods of treatment are offered for this purpose. The inventions make it possible to create a new drug with a well-balanced receptor profile, the intake of which will allow to treat mental disorders in an effective way without causing side effects associated with exposure to receptors that are not involved in the pathology of a mental disorder.

8 Claims, 5 Drawing Sheets (56) References Cited

OTHER PUBLICATIONS

Liu et al., "Clozapine is Oxidized by Activated Human Neutrophils to a Reactive Nitrenium Ion that Irreversibly Binds to the Cells" *The Journal of Pharmacology and Experimental Therapeutics*, vol. 275, No. 3: 1476-1483 (1995).
Ng et al., "Effect of Aminoglutethimide on Neutrophils in Rats: Implications for Idiosyncratic Drug-Induced Blood Dyscrasias" *Chemical Research in Toxicology*, vol. 26: 1272-1281 (2013).
Rosenheck et al., "How Long to Wait for a Response to Clozapine: a Comparison of Time Course of Response to Clozapine and Conventional Antipsychotic Medication in Refractory Schizophrenia" *Schizophrenia Bulletin*, vol. 25, No. 4: 709-719 (1999).
Schaber et al., "Isolation and Identification of Clozapine Metabolites in Patient Urine" *Drug Metabolism and Disposition*, vol. 29, No. 6: 923-931 (2001).
Shekhar et al., "Selective Muscarinic Receptor Agonist Xanomeline as a Novel Treatment Approach for Schizophrenia" *Am J Psychiatry*, vol. 165: 1033-1039 (Aug. 2008).
Spina et al., "Relationship between plasma concentrations of clozapine and norclozapine and therapeutic response in patients with schizophrenia resistant to conventional neuroleptics" *Psychopharmacology* (Berl), vol. 148: 83-89 (2000).
Wahlbeck et al., "Clozapine versus typical neuroleptic medication for schizophrenia (Review)" *Cochrane Database Syst Rev*, 63 pages, (2008) CD000059.
Williams et al., "Neutrophil Cytotoxicity of the Chemically Reactive Metabolite(s) of Clozapine: Possible Role in Agranulocytosis" *The Journal of Pharmacology and Experimental Therapeutics*, vol. 283, No. 3: 1375-1382 (1997).
Ben-Aryeh et. al., "Salivary Flow-Rate and Composition in Schizophrenic Patients on Clozapine: Subjective Reports and Laboratory Data" *Biol Psychiatry*, 1996, 39: 946-949.
Fisher, "Cholinergic Treatments with Emphasis on MI Muscarinic Agonists as Potential Disease-Modifying Agents for Alzheimer's Disease" *Neurotherapeutics: The Journal of the American Society for Experimental NeuroTherapeutics*, 2008, 5: 433-442.
Guest et al., "Drugs that induce neutropenia/ agranulocytosis may target specific components of the stromal cell extracellular matrix" *Medical Hypotheses*, 1999, 53(2): 145-151.
Iverson et al., " Effect of Clozapine on Neutrophil Kinetics in Rabbits" *Chem. Res. Toxicol.*, 2010, 23: 1184-1191.

*Klozapin, Entsiklopediya Lekarstv, Rls 8-e izd., Moscow, 2001, pp. 421-422.
Leucht et. al., "Comparative efficacy and tolerability of 15 antipsychotic drugs in schizophrenia: a multiple-treatments meta-analysis" *Lancet*, 2013, 382: 951-962.
Liu et al., "Clozapine is Oxidized by Activated Human Neutrophils to a Reactive Nitrenium Ion that Irreversibly Binds to the Cells" *the Journal of Pharmacology and Experimental Therapeutics*, 1995, 275(3): 1476-1483.
Ng et al., "Effect of Aminoglutethimide on Neutrophils in Rats: Implications for Idiosyncratic Drug-Induced Blood Dyscrasias" *Chem. Res. Toxicol.*, 2013, 26: 1272-1281.
Paraschakis A., Pipamperone augmentation of clozapine and sodium valproate in refractory schizophrenia: a case report. Clin. Neuropharmacol., Mar.-Apr. 2014; vol. 37, No. 2, pp. 60-61.
*Prim Care Companion J Clin Psychiatry*, "A Roadmap to Key Pharmacologic Principles in Using Antipsychotics," 2007, 9(6): 444-454.
Sanyal et al., "Review the Role of Dopamine D4 Receptors in Schizophrenia and Antipsychotic Action" *J Psychiatr Res*, 1997, 31(2): 219-232.
Seeman et al., "Schizophrenia: More dopamine, more D2 receptors" *Proc Natl Acad Sci, U S A.*, 2000, 97(14): 7673-7675.
Shekhar et al., "Selective Muscarinic Receptor Agonist Xanomeline as a Novel Treatment Approach for Schizophrenia" *Am J Psychiatry*, 2008, 165(8): 1033-1039.
Sovremennaya Meditsinskaya Entsiklopediya, Saint Petersburg, "NORIT", 2004, p. 333.
Travis et al., "5HT$_{2A}$ receptor blockade in patients with schizophrenia treated with risperidone or clozapine, a SPET study using the novel 5-HT$_{2A}$ ligand $^{123}$I-5-I-R-91150" *Br J Psychiatry*, 1998, 173: 236-241.
Williams et al., "Neutrophil Cytotoxicity of the Chemically Reactive Metabolite(s) of Clozapine: Possible Role in Agranulocytosis" *The Journal of Pharmacology and Experimental Therapeutics*, 1997, 283(3): 1375-1382.
International Search Report issued in PCT/RU2016/000783 dated Mar. 16, 2017.
International Preliminary Report on Patentability issued in PCT/RU2016/000783 dated Sep. 4, 2018.
Barrus et al., "Disadvantageous decision-making on a rodent gambling task is associated with increased motor impulsivity in a population of male rats," Journal of psychiatry & neuroscience: JPN 40.2 (2015): 108, 10 pages.

* cited by examiner

PHARMACEUTICAL COMPOSITION FOR TREATING FUNCTIONAL PSYCHIATRIC DISORDERS

This application is the U.S. national phase of International Application No. PCT/RU2016/000783 filed 15 Nov. 2016, which designated the U.S. and claims priority to RU patent application No. 2016107968 filed 4 Mar. 2016, the entire contents of each of which are hereby incorporated by reference.

The invention relates to medicine, pharmacology, namely to psychiatry and can be used for effective and safe treatment of mental disorders associated with dysfunction of dopamine and serotonin (5-hydroxytryptamine) neurotransmitter systems.

BACKGROUND OF THE INVENTION

Currently, mental health is one of the most serious challenges all countries have to deal with, since at least every fourth person faces such problems during a lifetime. Prevalence of mental health disorders in the European Region is very high. According to the WHO (2006), about 4 of 870 million people in the European Region suffer from schizophrenia; 4 million—from bipolar affective disorders, and 4 million—from panic disorders.

Mental disorders represent the second (after cardiovascular diseases) major cause of disease burden. Their share takes up to 19.5% of DALYs (disability-adjusted life years). More than 40% of all chronic diseases are mental disorders.

Pharmacological treatment of mental disorders is based on blocking the receptors that regulate the propagation of nerve impulses in the brain. However, mental disorders, including schizophrenia and bipolar disorder, are polymorphic diseases, characterized by a huge variety of symptoms of the disease and variants of its progress, and currently exact causes and mechanisms of disease development are not identified. It has been established that the drugs used in the treatment of mental disorders, in particular, schizophrenia, should have a well-balanced receptor profile: to affect receptors directly involved in the disease pathology; to inhibit receptors associated with certain specific manifestations of the disease pathology and, when applicable, not to affect receptors whose inhibition or activation leads to undesired side effects.

One of the most important families of receptors that are involved in the pathology of schizophrenia and other mental disorders is the family of dopamine receptors (Prim Care Companion J Clin Psychiatry. 2007; 9(6):444-54). According to the dopamine hypothesis of disease, etiology of the disease is associated with increased stimulation of dopamine receptors (Proc Natl Acad Sci USA., 2000, 97(14): 7673-7675). Among the dopamine receptors, D2 receptor plays an important role. It was found that the effectiveness of antipsychotics (haloperidol, risperidone) correlates with the effectiveness of drug interactions with D2 receptor. However, prolonged use of such drugs is associated with a large number of side effects (incl. irreversible effects). For the next generation of antipsychotics, including the most effective antipsychotic drug named clozapine, binding to D2 receptor is low and inferior to another member of the dopamine receptor family—D4 (J Psychiatr Res. 1997; 31(2):219-32). Studies of D2 receptor occupancy in patients taking antipsychotics have shown that blockade of D2 receptors increases the risk of the central nervous system side effects (convulsions, delayed dyskinesia, akathisia). Therefore, the goal in the development of new drugs is to achieve a high antipsychotic effect without significant effect on D2 receptors.

Another area of impact on mental disorders is a blockade of serotonin receptors. One of the most important disease targets are 5HT2A serotonin receptors. Activators of this receptor include drugs that cause hallucinations, including psilocybin, LSD, mescaline. Presumably, an increase in the level of expression and increased activation of 5HT2A serotonin receptor leads to the emergence of so-called positive symptoms of schizophrenia, including delusion, visual and auditory hallucinations. Many atypical antipsychotics (clozapine, risperidone) are antagonists of serotonin receptors, but most of them are not sufficiently selective, so the effect on serotonin 5HT2A receptor and antihallucinatory effect are observed only in high doses, when the drug administration is complicated by the presence of other side effects (Br J Psychiatry. 1998 September; 173:236-4).

Another problem encountered in the treatment of mental disorders is sedation. Sedation is a common side effect of antihistamines, the histamine H1 receptor antagonists that penetrate the blood-brain barrier. Sedation is the reason for using diphenhydramine (dimedrol) and doxylamine antihistamines as remedies against insomnia. Sedation caused by the effect on histamine receptors is a side effect of most antipsychotic drugs. For example, the intake of clozapine increases the risk of sedation by 8.8 times, olanzapine intake by 3.3 times, quetiapine intake by 3.7 times (Leucht, S. et. al., Lancet, 2013, 382, 951-62).

Other receptors, the effect on which cause side effects when taking known antipsychotic drugs, include the family of muscarinic receptors. In particular, the side effect of M4 muscarinic receptor agonists is intense salivation (sialorrhea). Sialorrhea occurs in 30% of patients taking clozapine (Ben-Aryeh, H. et. al., Biol Psychiatry, 1996, 39, 946-9) and is one of the main reasons for refusal to take the drug.

Thus, there is a problem of creating an antipsychotic drug selectively influencing the main receptors associated with the pathology of mental disorders.

SUMMARY OF THE INVENTION

The object of this invention is to create a new drug having a well-balanced receptor profile, the use of which allows to treat mental disorders in an effective way and does not cause side effects associated with exposure to receptors that are not involved in the pathology of a mental disorder.

This problem is solved by the development of a pharmaceutical composition comprising a compound with the formula (I)

where R1 is a halogen,
R2 is H or $C_1$-$C_3$-alkyl
or its pharmaceutically acceptable salt, hydrate or solvate in an amount effective as selective antagonists of D4 and 5HT2A receptors, and at least one pharmaceutically acceptable carrier.

In some embodiments of the invention the selective D4 receptor antagonist is characterized in that a ratio of D2/D4 binding constants is greater than 1.5.

In some embodiments of the invention the selective D4 receptor antagonist is characterized in that a ratio of D2/D4 binding constants is greater than 4.

In some embodiments of the invention the selective 5HT2A receptor antagonist is additionally characterized in that a ratio of D2/5HT2A binding constants is greater than 10.

In particular embodiments of the invention the selective 5HT2A receptor antagonist is additionally characterized in that a ratio of D2/5HT2A binding constants is greater than 30.

In some embodiments of the invention the selective 5HT2A receptor antagonist is additionally characterized in that a ratio of H1/5HT2A binding constants is greater than 0.5.

In some embodiments of the invention the selective D4 and 5HT2A receptor antagonists are not agonists of M4 muscarinic receptor.

In some embodiments of the invention, R1 is fluorine.

In some embodiments of the invention, R2 is H or CH$_3$.

In particular embodiments of the invention, the compound according to the formula (I) is 11-(piperazine-1-yl)-7-fluoro-8-chloro-3-ethyl-5H-dibenzo[b,e][1,4]diazepine or 11-(4-methylpiperazine-1-yl)-7-fluoro-8-chloro-5H-dibenzo[b,e][1,4]diazepine.

In some embodiments of the invention, the effective amount of the compound according to the formula (I) providing selective blockade of D4 and 5NT2A receptors ranges from 0.14 mg/kg to 11.5 mg/kg per day.

In some embodiments of the invention, the effective amount of the compound according to the formula (I) providing selective blockade of D4 and 5NT2A receptors ranges from 10 mg to 800 mg per day.

In particular embodiments of the invention, the effective amount of formula (I) compound ranges from 50 mg to 600 mg per day.

In some embodiments of the invention, the effective amount of formula (I) compound ranges from 70 mg to 200 mg per day.

The intended objective is also achieved by using the above pharmaceutical composition for the treatment of conditions requiring selective inhibition of D4 and 5HT2A receptors.

In some embodiments of the invention, one of the conditions requiring selective inhibition of D4 and 5HT2A receptors is schizophrenia.

In some particular embodiments of the invention, schizophrenia is understood to mean a treatment-resistant schizophrenia.

In some other embodiments of the invention, one of the conditions requiring selective inhibition of D4 and 5HT2A receptors is bipolar disorder.

In some other embodiments of the invention, one of the conditions requiring selective inhibition of D4 and 5HT2A receptors is impulsivity (including pathological gambling disorder).

In some other embodiments of the invention, one of the conditions requiring selective inhibition of D4 and 5HT2A receptors is psychotic depression.

In some other embodiments of the invention, one of the conditions requiring selective inhibition of D4 and 5HT2A receptors is the risk of exacerbation of a mental disorder pathology or the risk of deterioration in quality of life due to a mental disorder.

The intended objective is also achieved by a method for treating a condition requiring selective inhibition of D4 and 5HT2A receptors comprising administering to a patient the above pharmaceutical composition.

In some embodiments of the invention, the effective amount of formula (I) compound in the pharmaceutical composition ranges from 10 mg to 800 mg per day.

In particular embodiments of the invention, the effective amount of formula (I) compound in the pharmaceutical composition ranges from 50 mg up to 600 mg per day.

In particular embodiments of the invention, the effective amount of formula (I) compound in the pharmaceutical composition ranges from 70 mg up to 200 mg per day.

In some embodiments of the invention, the pharmaceutical composition is administered as a daily dose once a day.

In some embodiments of the invention, the pharmaceutical composition is administered twice a day.

In some embodiments of the invention, the pharmaceutical composition is administered three times a day.

In some embodiments of the invention, the pharmaceutical composition is administered within two weeks.

In some embodiments of the invention, the pharmaceutical composition is administered until the recovery of the condition requiring inhibition of D4 receptor and selective inhibition of 5HT2A receptor.

In some embodiments of the invention, the pharmaceutical composition is administered within the period from 1 to 10 years.

In some embodiments of the invention, the pharmaceutical composition is administered throughout the patient's life.

Technical results achieved by a group of inventions:

Provision of new pharmaceutical compositions containing therapeutically effective amounts of the active ingredient, which is both a selective antagonist of D4 and 5HT2A receptors, and methods of treating conditions requiring inhibition selective inhibition of D4 and 5HT2A receptors.

Improvement of the treatment effectiveness for conditions requiring selective inhibition of D4 and 5HT2A receptors due to more effective inhibition of the above target receptors, which in turn leads to a decrease in the minimum effective dose of the active ingredient.

Reduction of side effects in the treatment of conditions requiring selective inhibition of D4 and 5HT2A receptors due to selective action on the target receptors and reduced activity or due to the lack of activity against non-target D2, H1 and M4 receptors, which in turn leads to an increase in the maximum tolerated dose of the active ingredient.

Expanding the therapeutic window of the active ingredient of pharmaceutical compositions, which in turn provides wider opportunities in choosing a treatment regimen corresponding to the needs of the patient depending on the nosology, and severity level of the patient's condition, its duration, phase and other factors.

In particular embodiments, the group of inventions allows to achieve a reduction in the drug burden and the probability of occurrence of undesired drug interactions in the combination therapy. In particular embodiments, the group of inventions allows to achieve a therapeutic effect for the forms of conditions which are resistant to another therapy.

TERMS AND DEFINITIONS

Antagonist (receptor antagonist) in biochemistry and pharmacology is a subtype of ligands of intracellular receptors. A ligand with properties of the receptor antagonist is a ligand that inhibits, blocks, reduces or prevents physiological effects caused by binding an agonist (incl. an endogenous agonist) to the receptor.

Selective antagonist is one that inhibits a specific receptor or subtype of receptors. The level of selectivity may vary.

The term "pharmaceutically acceptable salts" used herein includes salts of active compounds which have been prepared with relatively non-toxic acids or bases. Examples of pharmaceutically acceptable non-toxic salts include salts formed with inorganic acids such as hydrochloric, hydrobromic, phosphoric, sulfuric and perchloric acids, or with organic acids such as acetic, oxalic, maleic, tartaric, succinic, citric or malonic acids or resulting from other methods used in this field, for example, by ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentane propionate, digluconate, dodecyl sulfate, ethanesulfonate, formate, fumarate, glucoheptonate, glycerophosphate, gluconate, hemisulphate, heptanate, hexanate, hydroiodide, 2-hydroxyethanesulfonate, lactobionate, lactate, laurate, lauryl sulfate, malate, maleate, malonate, methanesulfonate (mesylate), 2-naphthalenesulfonate, nicotinate, nitrate, oleate, oxalate, palmitate, pamoate, pectinate, persulfate, 3-phenylpropionate, phosphate, picrate, pivalate, propionate hemifumarate, stearate, succinate, sulfate, tartrate, thiocyanate, p-toluenesulfonate (tosylate), undecanoate, valerate, and the like.

Solvate means an association or complex of solvent molecules and compounds according to the invention. Examples of solvents that form solvates include, but are not limited to, water, isopropanol, ethanol, methanol, DMSO, ethyl acetate, acetic acid and ethanolamine. The term "hydrate" refers to a complex where molecules of solvent are water molecules.

A condition requiring selective inhibition of D4 and 5HT2A receptors is a mental disorder associated with the derangement of dopamine and serotonin neurotransmitter systems.

Mental disorder (functional mental disorder) means a medical condition in which there is a disturbance in mood, thinking, perception, the ability to cope with everyday stress, to react adequately to the situation, to verify the correctness of own impressions, judgments and behaviour with signals received from objective reality. These disorders appear due to damage to brain tissue, i.e., they are manifestations of disturbed mental processes, but not a visible structural defect of the brain.

Examples of mental disorders associated with disorders of dopamine and serotonin neurotransmitter systems include, but are not limited to, schizophrenia, including forms of treatment-resistant schizophrenia, bipolar disorder, impulsivity, including pathological gambling disorder, psychotic depression.

The invention also relates to pharmaceutical compositions which contain at least one of the compounds described herein (or a prodrug, a pharmaceutically acceptable salt or other pharmaceutically acceptable derivative) and one or more pharmaceutically acceptable carriers, solvents and/or excipients. Pharmaceutical compositions according to the present invention can be used both as monotherapy and administered to a patient in need of appropriate therapy in combination with one or more other therapeutic agents.

Pharmaceutical compositions according to the present invention contain compounds as active ingredient together with pharmaceutically acceptable carriers, which may include any solvents, diluents, dispersions or suspensions, surfactants, isotonic agents, thickeners and emulsifiers, preserving agents, binding agents, lubricants, etc., suitable for the particular form of dosage. Except for cases, when the medium of conventional carriers is incompatible with the active ingredient, for example, upon occurrence of any undesirable biological effects or other adverse interactions with any other ingredient(s) of the pharmaceutical composition, the use of such compositions falls within the scope of this invention. Materials that can serve as pharmaceutically acceptable carriers include, but are not limited to, monosaccharides and oligosaccharides, as well as derivatives thereof; malt, gelatin; talc; excipients such as: cocoa butter and suppository waxes; oils, such as peanut oil, cottonseed oil, safflower oil, sesame oil, olive oil, corn oil and soybean oil; glycols such as propylene glycol; esters, such as ethyl oleate and ethyl laurate; agar; buffering agents, such as magnesium hydroxide and aluminium hydroxide; alginic acid; pyrogen-free water; isotonic saline, Ringer's solution; ethyl alcohol and phosphate buffer solutions. In addition, the composition may contain other non-toxic compatible lubricants, for example such as sodium lauryl sulfate and magnesium stearate, as well as coloring agents, parting liquids, film formers, sweeteners, flavoring additives and flavorants, preserving agents and antioxidants.

The compounds described herein can also be used for the production of drugs for treatment of mental diseases associated with the derangement of dopamine and serotonin neurotransmitter systems.

Drug formulations, a class of pharmaceutical compositions, the contents of which is optimized for a particular route of administration in a therapeutically effective dose, are also the subject matter of the invention. Pharmaceutical compositions according to this invention allow for the following ways of administration: oral or parenteral, including topical, intravascular (including infusion administration), intranasal, intraperitoneal, subcutaneous, intramuscular, transdermal (including administration by transdermal therapeutic systems) according to recommended dosages. Drug formulations according to the invention may contain compositions prepared by means of the use of liposomes or methods of microencapsulation, methods of preparing drug nanoparticles and other examples, which are known in the pharmaceutics.

The subject of the present invention also includes administering to a trial subject in need of appropriate treatment an effective amount of the pharmaceutical composition according to the invention.

The term "effective amount" means an amount that causes selective inhibition of target receptors. The exact amount required may vary from subject to subject depending on the mammalian species, age and general condition of the patient, disease severity, drug administration technique, combined treatment with other drugs, etc.

A pharmaceutical composition containing the active ingredient can be administered to the patient in any amount and any administration way, effective for the selective inhibition of target receptors and treatment of the conditions requiring selective inhibition of D4 and 5HT2A receptors, namely, mental disorders associated with disorders of dopamine and serotonin neurotransmitter systems.

Single doses of the drug are preferably formulated in a form suitable for administration to a patient. "Single dose" in terms of the present invention means a portion of the active ingredient suitable for treatment of a condition requiring selective inhibition of D4 and 5HT2A receptors, namely, a mental disorder associated with disorders of dopamine and serotonin neurotransmitter systems.

According to current practice, the total daily dose of pharmaceutical compositions described in the present invention is prescribed by the attending physician based on the medical opinion. The specific therapeutically effective dosage level for each individual patient depends on a number of factors, including type of disorder, severity of disease, activity of the specific active ingredient, characteristics of the pharmaceutical composition, age, body weight, general health condition, patient gender and diet, method and schedule of drug administration, the rate of metabolism and/or excretion of the active ingredient, the duration of treatment, the drugs used in combination or in conjunction with the administration of the pharmaceutical composition according to the invention, and other factors well known in medicine.

After mixing the active component with a specific suitable pharmaceutically acceptable carrier in the desired dosage, the compositions constituting the essence of the invention can be administered to a patient or animals orally, rectally, parenterally, intraperitoneally, topically (with skin patches, powders, unctures or drops), sublingually, buccally, in the form of a spray for the mouth or nose, etc.

The composition can be administered both once and several times a day, a week (or any other time interval), or from time to time. For example, a pharmaceutical composition can be administered to a patient one or more times a day on a weekly basis (e.g. every Monday) for an indefinite time period or for several weeks (e.g. 4-10 weeks).

In the case where the active ingredient according to the present invention is used as part of a combination therapy regimen, the dose of each components of combination therapy is administered during the required treatment period. The active ingredients comprising the combination therapy can be administered to a patient both once, in the form of a dosage containing all the components, and in the form of individual dosages of the components; in addition, the active ingredients of the combination therapy can be administered to a patient at different times during the treatment period, or one of the active ingredients can be administered as a pre-treatment for another.

DETAILED DESCRIPTION OF THE INVENTION

Pre-clinical studies and clinical trials of selective ligands of G-protein-coupled receptors (GPCR) allow to relate both their efficiency and side effects to the influence on individual receptors. Following the functional studies carried out on the receptor panel in vitro, it has been found that the introduction of halogen atom into the 7th position of dibenzo[b,e][1,4]diazepine ring of clozapine and its derivatives by substituents of the nitrogen atom in the 4th position of the piperazine ring substantially modifies the interaction with dopamine, serotonin, histamine and muscarinic receptors. Surprisingly, this structural modification led to a significant expansion of the therapeutic window of such halogen derivatives in comparison with other known antipsychotic drugs, which is not observed when other substituents are introduced into 7th position or a halogen atom is introduced into other positions. The expansion of the therapeutic window is associated both with a significant reduction in the risk of developing a number of direct side effects due to effect on receptors that are not involved in the pathology of a mental disorder, and with an increase in the efficiency of the relief of a mental disorder due to effective action on receptors associated with the manifestations of this pathology.

At the same time, our studies have unexpectedly shown that the introduction of a halogen atom into the 7th position of dibenzo[b,e][1,4]diazepine ring of clozapine and its derivatives by substituents of the nitrogen atom in the 4th position of the piperazine ring prevents the formation of toxic metabolites in the human body, the formation of which occurs during the treatment with clozapine, and which is the cause of agranulocytosis in some patients. Most likely, a significant decrease in toxicity is due to the fact that the introduction of a halogen atom into the 7th position prevents the most probable way of oxidation of the benzodiazepine nucleus in the human body. In addition, the acceptor properties of the introduced substituent reduce the reactivity of the nitrenium ion, and consequently lead to a decrease in the toxicity of oxidation products of compounds and their metabolites in comparison with clozapine and N-desmethylclozapine.

General Scheme for the Synthesis of Compounds

The compounds according to the present invention can be prepared using the synthetic methods described below. These methods are not exhaustive and allow the introduction of reasonable modifications. The shown reactions should be carried out using suitable solvents and materials.

It shall be understood that these and all examples given in the application materials are not restrictive and are given only to illustrate the present invention.

At the first stage, the nitration of compound (1) produces compound (2), which, when heating with 2-aminobenzonitrile in the presence of KF for 5-6 days at 150-160° C. in a polar aprotonic solvent forms a nitro-derivative compound (3). Reduction of the nitro group (3) is performed with sodium dithionite in a relevant solvent with obtaining the intermediate product (4). Ring formation is carried out under acid conditions with the formation of compound (5), which is crystallized followed by isolation of the salt (6). The reaction of compound (6) with an amino derivative in which the substituent R2 is hydrogen or $C_{1-3}$ alkyl in an aprotonic solvent (DMSO, toluene), produces the end product (7).

Examples of the Synthesis of Specific Compounds

Example 1

11-(4-methylpiperazine-1-yl)-7-fluoro-8-chloro-5H-dibenzo[b,e][1,4] diazepine(fluoroclosapine, FClo) can be synthesized from 11-amino-7-fluoro-8-chloro-5H-dibenzo[b,e][1,4] diazepine (compound (5) of the general synthesis scheme) according to the following scheme:

64.9 g of compound 1 in 450 ml of diethyl ether are added to a two-liter flat-bottom flask equipped with a magnetic stir bar and a backflow condenser. 124 ml of 3M HCl in dioxane are added to the resulted suspension. The reaction mass is stirred for 30 minutes. The formed crystals are filtered off, squeezed and washed on the filter with two 150 ml portions of diethyl ether. Yield of compound 2 is 73 g, 98% of the theoretical value.

98 g of compound 2 are dissolved in a mixture of toluene:dmso=490:490 ml in a two-liter flat-bottom flask equipped with a magnetic stir bar and a backflow condenser followed by the addition of 291.7 ml of methylpiperazine. The instrument is purged with argon, supply of inert gas from the cylinder is stopped (leaving the balloon filled with argon) and the reaction mass is boiled for 36 hours. TLC monitoring (dichloromethane:methanol=20:1).

The reaction mass is poured into water and extracted three times with ethyl acetate in 150 ml portions. The combined organic layer is washed with three 150 ml portions of water. It is dried over sodium sulfate and the solvent is distilled in the rotary film evaporator. 500 ml of methanol are added to the distillation residue, and the mixture is stirred with the use of mechanical stirrer for 10 minutes. The precipitated crystals are filtered off, squeezed and washed on the filter with 100 ml of methanol.

Product 3 is purified by recrystallization from methanol with activated carbon, calculating the volume of solvent per 1 g of product, 15 ml of methanol and 10% of the mass of compound 3 of activated carbon.

Yield: 59 g, 61%.

$^1$H NMR (DMSO-d$_6$, 400 MHz) δ, ppm 2.198 (s, 3H, N—CH$_3$), 2.371 (br. s, 4H, 2 CH$_2$ piperazine), 3.286 (br. s, 4H, 2 CH$_2$ piperazine), 6.886 (d, 1H, J=10.4 Hz), 6.954 (d, 1H, J=8.0 Hz), 7.00-7.04 (m (d+t), 2H), 7.188 (d, 1H, J=8.0 Hz), 7.3-7.37 (m (s+t), 2H).

Example 2

11-(piperazine-1-yl)-7-fluoro-8-chloro-5H-dibenzo[b,e][1,4]diazepine (desmethylfluoroclozapine, dFClo) can be synthesized from 11-amino-7-fluoro-8-chloro-5H-dibenzo[b,e][1,4] diazepine (compound (5)) of the general synthesis scheme) according to the following scheme:

63 g of compound 2 are dissolved in a mixture of toluene:dmso=315:315 ml in a two-liter flat-bottom flask equipped with a magnetic stir bar and a backflow condenser followed by the addition of 145.6 ml of piperazine. The instrument is purged with argon, supply of inert gas from the cylinder is stopped (leaving the balloon filled with argon) and the reaction mass is boiled for 36 hours. TLC monitoring (dichloromethane:methanol=20:1). Then the mixture is cooled to indoor temperature and poured into 2 liters of water. After that, it is extracted in three 200 ml portions of ethyl acetate. The combined organic layers are washed with three 100 ml portions of water. Then the organic layer is dried over sodium sulfate.

The organic phase is filtered through a 10 mm silica gel layer and washed on the filter with 2 liters of ethyl acetate. The mother liquor is extracted with 4 M hydrochloric acid solution in water. After that, the aqueous phase is washed with three 150 ml portions of ethyl acetate.

Then, upon cooling, the aqueous phase is alkalized with pre-cooled 4M NaOH solution to adjust pH to 10. The precipitated crystals are filtered off, squeezed and washed on the filter with three 150 ml portions of water. The resulting product 4 is recrystallized from toluene (ethanol, methyl ethyl ketone), calculating the volume of solvent: 3 ml of solvent per 1 g of the product.

Yield: 45 g, 50%.

$^1$H NMR (DMSO-d$_6$, 400 MHz) δ, ppm 2.748 (br. s, 4H, 2 CH$_2$ piperazine), 3.225 (br. s, 4H, 2 CH$_2$ piperazine), 6.884 (d, 1H, J=10.4 Hz), 6.941 (d, 1H, J=8.0 Hz), 7.00-7.04 (m (d+t), 2H), 7.197 (d, 1H, J=8.0 Hz), 7.3-7.37 (m (s+t), 2H).

The possibility of objective demonstration of the technical result while using the invention has been confirmed by reliable data outlined in the examples and containing the experimental data obtained in the process of research following the procedures recognized in the art. The essence of the invention is also illustrated with drawings.

Example 1

Expanded Therapeutic Window of D2/D4.4

Dimensions of the therapeutic window for clozapine and its halogen derivatives were estimated by the ratio of binding constants (Kb) of D2 and D4 dopamine receptors, which were determined by IC$_{50}$ values for the corresponding receptors in the antagonism experimental setup. Response for cells expressing D2 receptors was determined as the change in cell conductance caused by the redistribution of intracellular calcium. For D4 receptor, the response criterion was the level of the secondary messenger, cAMP, determined by fluorescence after lysis of the cell expressing the receptor.

Figure 1:
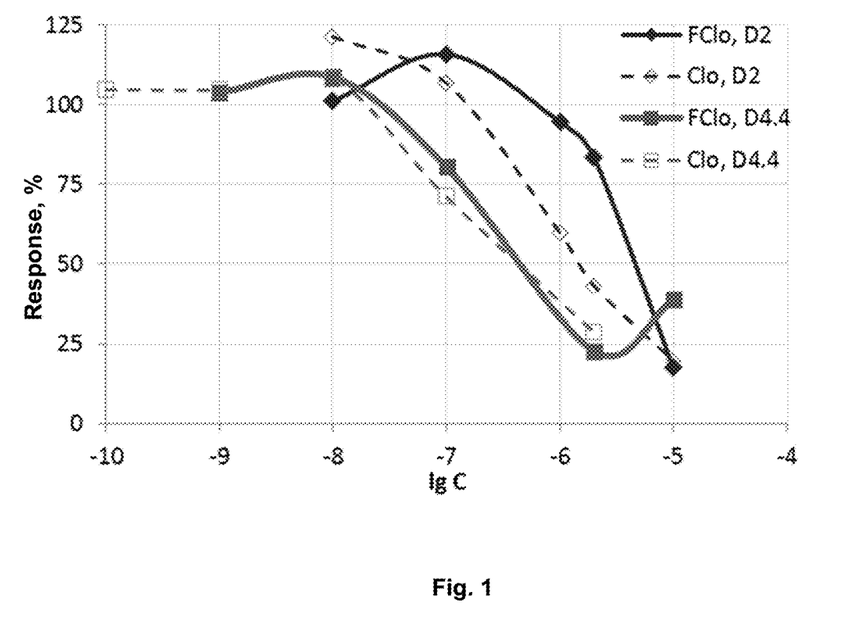
FIG. 1. Dependence of the functional response (Response, %) on the concentration of fluoroclosapine (FClo) and clozapine (Clo) drugs for D2 and D4.4 receptors.
Figure 2:
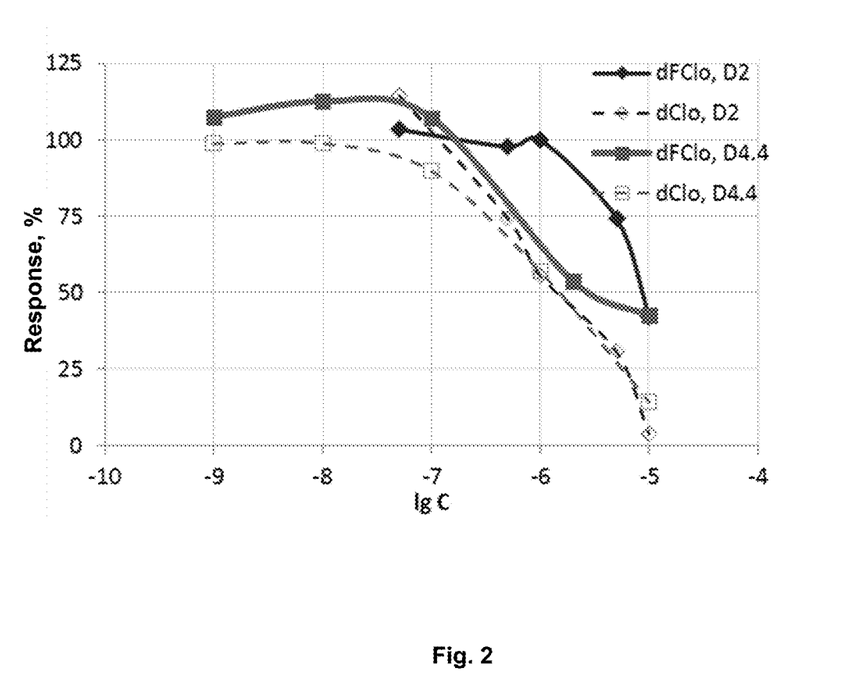
FIG. 2. Dependence of the functional response (Response, %) on the concentration of desmethylfluoroclozapine (dFClo) and desmethylclozapine (dClo) drugs under test for D2 and D4.4 receptors.

FIGS. 1 and 2 show the dependence of the response on the concentration of the drugs under test. Studies have shown that halogen derivatives of clozapine have a large interval of concentrations which exhibit activity against D4.4 receptor and do not exhibit activity against D2 receptor. The values of Kb and therapeutic window of compounds—ratios of Kb (D2)/Kb (D4.4) are given in the table:

|  | Kb (D2), μM | Kb (D4), μM | Therapeutic window width (Kb, D2/Kb, D4) |
| --- | --- | --- | --- |
| Fluoroclozapine | 0.26 | 0.05 | 5.2 |
| Desmethylfluoroclozapine | 0.55 | 0.35 | 1.6 |
| Clozapine | 0.057 | 0.047 | 1.2 |
| Desmethylclozapine | 0.052 | 0.19 | 0.27 |

The above data show that the halogen derivatives of clozapine, which are the active components of pharmaceutical compositions according to the invention, have a much wider therapeutic window for D2/D4.4 receptors compared to their closest structural analogues. Comparison of the data obtained with other known antipsychotics unexpectedly showed that the pharmaceutical compositions according to the invention are superior to other antipsychotics in the width of the therapeutic window of the active ingredient, for example, such drugs as quetiapine (Kb, D2/Kb,D4=0.11), olanzapine (Kb,D2/Kb,D4=0.53), risperidone (Kb,D2/Kb, D4=0.28) and haloperidol (Kb,D2/Kb,D4=0.37). This significant advantage of the pharmaceutical compositions according to the invention, comprising an effective amount of halogen derivatives of clozapine makes it possible to use them in the production of drugs for the treatment of mental diseases, whose use in clinical practice provide high antipsychotic activity and virtually eliminate the risk of a number of direct side effects such as extrapyramidal disorders, which in some cases are the cause of patients' refusal of treatment at the moment.

Example 2

Expanded Therapeutic Window of D2/5HT2A

As already mentioned, in addition to affecting the dopamine D4 receptor, another important target in the treatment of mental disorders are serotonin 5HT2A receptors, which are responsible, in particular, for the occurrence of hallucinations in mental disorders.

Inhibition of 5HT2A receptors is another important feature of the efficiency of antipsychotic drugs. However, the activity associated with antagonistic 5HT2A activity in inhibition of the dopamine D2 receptor leads to a significant narrowing of the therapeutic window and the possibility of using 5HT2A receptor antagonists in clinical practice.

In the experiments, the size of the therapeutic window of halogen derivatives of clozapine was evaluated by the ratio of binding constants (Kb) of serotonin 5HT2A receptor and dopamine D2 receptor, which were determined by $IC_{50}$ values for the respective receptors in the antagonism experimental setup. Response for cells expressing D2 receptors was determined by the change in cell conductance caused by the redistribution of intracellular calcium. For 5HT2A receptor, the response criterion was the level of the secondary messenger, cAMP, determined by fluorescence after lysis of the cell expressing the receptor.

Figure 3:
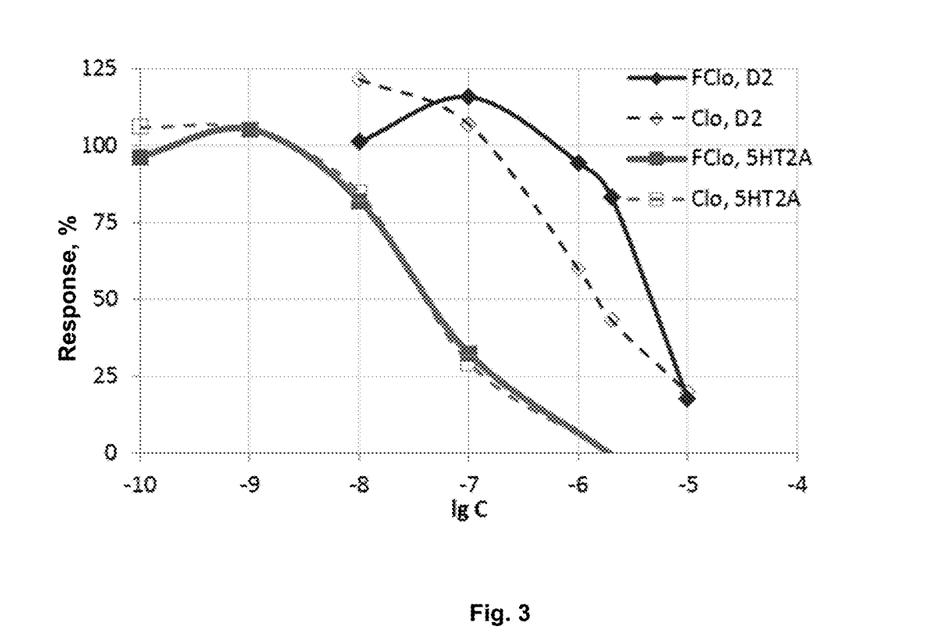
FIG. 3. Dependence of the functional response (Response, %) on the concentration of fluoroclosapine (FClo) and clozapine (Clo) drugs for D2 and 5HT2A receptors.
Figure 4:
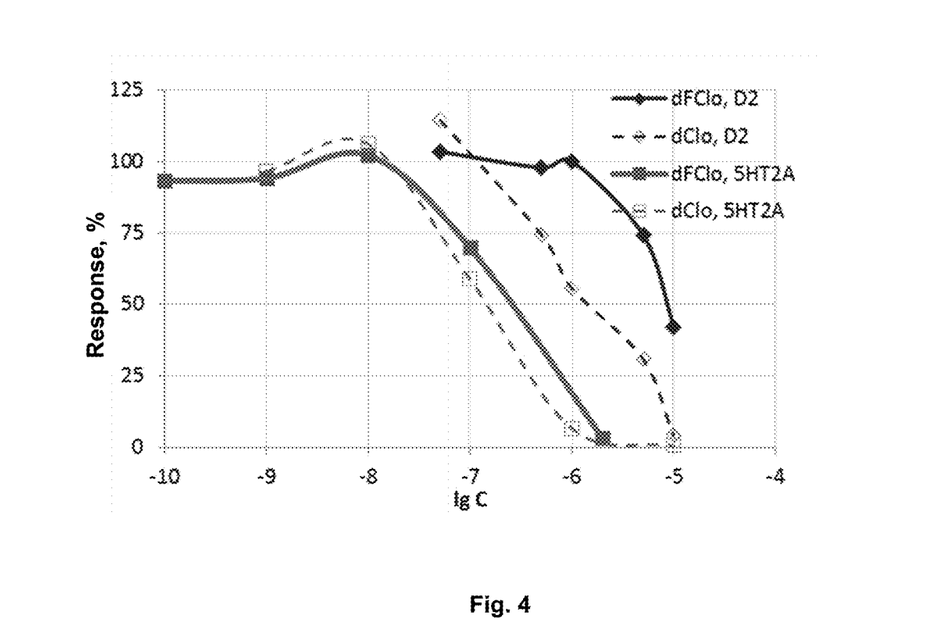
FIG. 4. Dependence of the functional response (Response, %) on the concentration of desmethylfluoroclozapine (dFClo) and desmethylclozapine (dClo) drugs for D2 and 5HT2A receptors.

FIGS. 3 and 4 show dependences of the functional response on the concentration of compounds under test in comparison with clozapine and desmethylclozapine. Studies have shown that halogen derivatives of clozapine have a large interval of concentrations which exhibit activity against 5HT2A receptor and do not exhibit activity against D2 receptor. The values of Kb and therapeutic window of compounds—ratios of Kb (D2)/Kb (5HT2A) are given in the table:

|  | Kb (D2), µM | Kb (5HT2A), µM | Therapeutic window width (Kb, D2/Kb, 5HT2A) |
| --- | --- | --- | --- |
| Fluoroclozapine | 0.26 | 0.0068 | 38 |
| Desmethylfluoroclozapine | 0.55 | 0.016 | 34 |
| Clozapine | 0.057 | 0.0055 | 10 |
| Desmethylclozapine | 0.052 | 0.015 | 3.5 |

These data indicate that the halogen derivatives of clozapine have a much wider therapeutic window of 5HT2A/D2 receptors in comparison with their structural analogues: ratio of D2/5HT2A binding constants for them is more than 30, while for clozapine it does not exceed 10. Such a significant advantage of the halogen derivatives of clozapine makes it possible to use them as an active ingredient of pharmaceutical compositions for the treatment of mental disorders, the use of which in clinical practice will provide high antipsychotic activity and virtually eliminate the risk of a number of direct side effects such as extrapyramidal disorders.

Conclusions: The summary data of the experiments described in Examples 1-2 showed not only a very high activity of halogen derivatives of clozapine against mental disorders due to effective antagonistic action on both D4 and 5HT2A receptors but also an unexpectedly low activity against D2 receptors, which eventually demonstrates that they have a substantially wider therapeutic window than other antipsychotic drugs and their closest structural analogues. This in turn is manifested in a wider range of therapeutically effective concentrations of halogen derivatives of clozapine as active ingredients of pharmaceutical compositions, which was further confirmed by animal experiments (see examples below).

Example 3

No Effect on the M4 Muscarinic Receptor

The side effect of M4 muscarinic receptor agonists is intense salivation (sialorrhea). Sialorrhea occurs in 30% of patients taking clozapine (Ben-Aryeh, H. et. al., Biol Psychiatry, 1996, 39, 946-9) and is one of the main reasons for refusal to take the drug. The binding of the halogen derivatives of clozapine according to the invention, as well as the binding of their closest structural analogues to the muscarinic M4 receptor, were under study in functional experiments. Curves of response dependence on the concentration of the compound for the receptor were built; the response criterion was the level of the secondary messenger—cAMP, which is determined by fluorescence after cell lysis expressing the receptor.

|  | $IC_{50}$, µM | $EC_{50}$, µM |
| --- | --- | --- |
| Fluoroclozapine | 4.8 | 16 |
| Desmethylfluoroclozapine | >10 | 3.2 |
| Clozapine | 0.11 | 0.011 |
| Desmethylclozapine | >10 | 0.098 |

Studies have shown that unlike its structural analogues, halogen derivatives of clozapine are unexpectedly weakly bind to M4 receptors. The activating concentration of fluoroclozapine (16 µM) falls outside the range of therapeutically achievable concentrations; activating concentration of desmethylfluoroclozapine (3.2 µM) is 30 times higher than that of desmethylclozapine and 290 times higher than the activating concentration of clozapine.

Example 4

Ratio of Inhibition of H1 and 5HT2A Receptors

Sedation due to the effect on histamine receptors is a side effect of most antipsychotic drugs. Thus, the intake of clozapine increases the risk of sedation by 8.8 times, olanzapine intake by 3.3 times, quetiapine intake by 3.7 times (Leucht, S. et. al., Lancet, 2013, 382, 951-62). Reduction of H1 receptor binding was a motivation for the development of new antipsychotic drugs (application PCT/162003/003583, Eli Lilly And Company, publ. on Feb. 19, 2004).

The interaction of halogen derivatives of clozapine, as well as the interaction of their closest structural analogues with the histamine receptors have been studied in functional experiments. The functional activity against H1 receptor was determined according to the fluorescence of Fluo-4 NW indicator introduced into cells, induced by a change in $Ca^{2+}$ ion concentration in the cytosol.

|  | $IC_{50}$, μM | Therapeutic window width (Kb, H1/Kb, 5HT2A) |
|---|---|---|
| Fluoroclozapine | 0.018 | 0.63 |
| Desmethylfluoroclozapine | 0.061 | 0.93 |
| Clozapine | 0.0059 | 0.25 |
| Desmethylclozapine | 0.015 | 0.24 |

Figure 5:
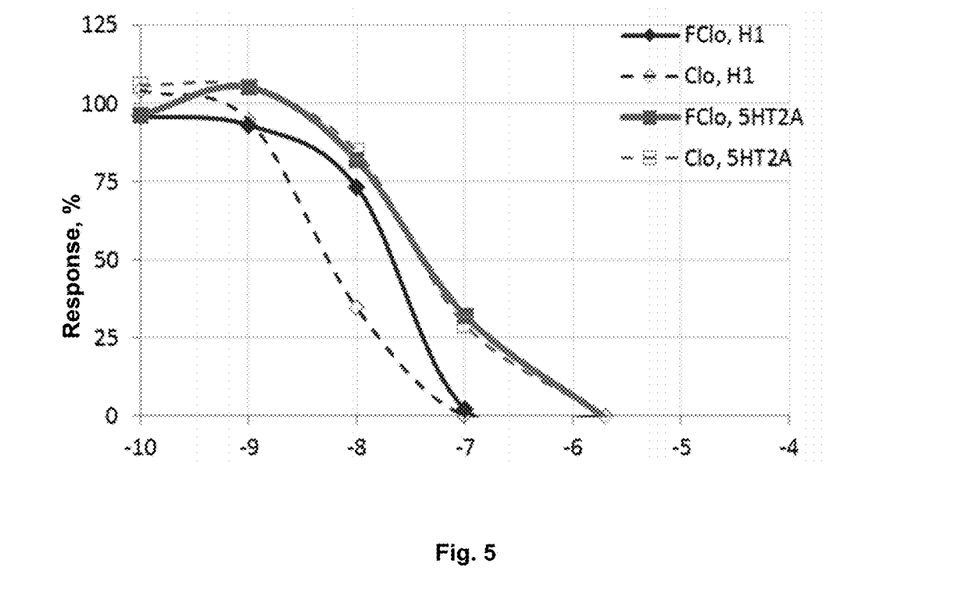
FIG. 5. Dependence of the functional response (Response, %) on the concentration of fluoroclosapine (FClo) and clozapine (Clo) drugs for 5HT2A and H1 receptors.

The study unexpectedly revealed that halogen derivatives of clozapine inhibit H1 receptor much weaker, and thus their use for the treatment of mental disorders in pharmaceutical compositions is expected to cause much lower sedation. Comparison of functional dependence on the cells expressing H1 and 5HT2A receptors (FIG. 5) shows that fluoroclozapine inhibits H1 and 5HT2A receptors in approximately equal concentrations, while clozapine inhibition of H1 occurs at concentrations 4 times lower than for inhibition of 5HT2A. Thus, the halogen derivatives of clozapine have a wider therapeutic window for 5HT2A/H1 receptors, which is another unexpected advantage of halogen derivatives of clozapine.

Example 5

No Effect on Adrenergic Receptors

In the course of further studies of activity of halogen derivatives of clozapine according to the invention on a panel of therapeutically relevant G-protein-coupled receptors, we found a relatively weak activity against the family of adrenergic receptors.

In conjunction with the results of preliminary toxicological studies, the data indicate a reduction in the risk of vegetative dysfunctions, such as tachysystole, orthostatism, accommodation disorder, gastrointestinal disturbances and urination dysfunction, weight gain, lack of coordination of muscle movements.

Example 6

Activation of M1 Muscarinic Receptors

It is known that activation of M1 muscarinic receptor has a procognitive effect. Thus, agonists of M1 muscarinic receptor are studied in clinical trials for the elimination of cognitive disorders and modification of the course of Alzheimer's disease and (Fisher, A., Neurotherapeutics, 2008, 5, 433-42) schizophrenia (Shekhar, A. et. al., Am J Psychiatry, 2008, 165, 1033-9).

Functional studies of ability of halogen derivatives of clozapine to activate M1 receptors have been conducted. The activity was determined according to the fluorescence of Fluo-4 NW indicator introduced into cells, induced by a change in $Ca^{2+}$ ion concentration in the cytosol.

Figure 6:
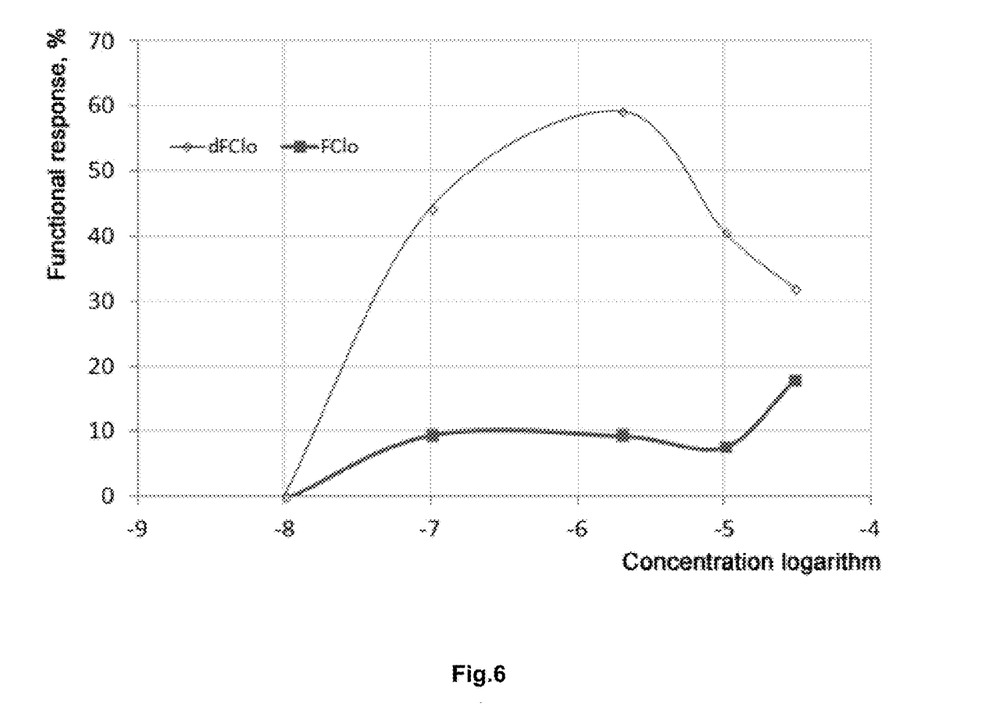
FIG. 6. Dependences of the functional response (relative level of second messengers in the cell) on the concentration of the test compounds (dFClo—desmethylfluoroclozapine, FClo—fluoroclozapine) in the in vitro test system for M1 receptor.

The resulting curves of the response dependence on the concentration for M1 receptor show that desmethylfluoroclozapine is an agonist, and causes a significant response in the therapeutic drug concentration window (FIG. 6). In the same experiment fluoroclozapine has shown virtually no effect on M1 receptors.

In addition, the metabolism and distribution of fluoroclozapine in tissues were studied. The concentration of fluoroclozapine and desmethylfluoroclozapine in tissues and organs (plasma, brain, heart, muscles, liver, kidneys, skin) of Sprague Dawley rats (n=6) was determined after single oral administration of fluoroclozapine at a dose of 10 mg/kg. The studies of metabolism have shown that fluoroclozapine is metabolized to desmethylfluoroclozapine in rats, and that the concentrations of fluoroclozapine and its metabolite desmethylfluoroclozapine in the brain are comparable.

Thus, as it follows from the experiments, after administration of fluoroclozapine its main metabolite is present in the brain at a concentration capable of causing the activation of M1 muscarinic receptors. This indicates that the halogen derivatives of clozapine according to the invention are effective for use in the treatment of cognitive disorders, including those accompanying mental disorders.

Example 7

Decreasing Sedation

Figure 7:
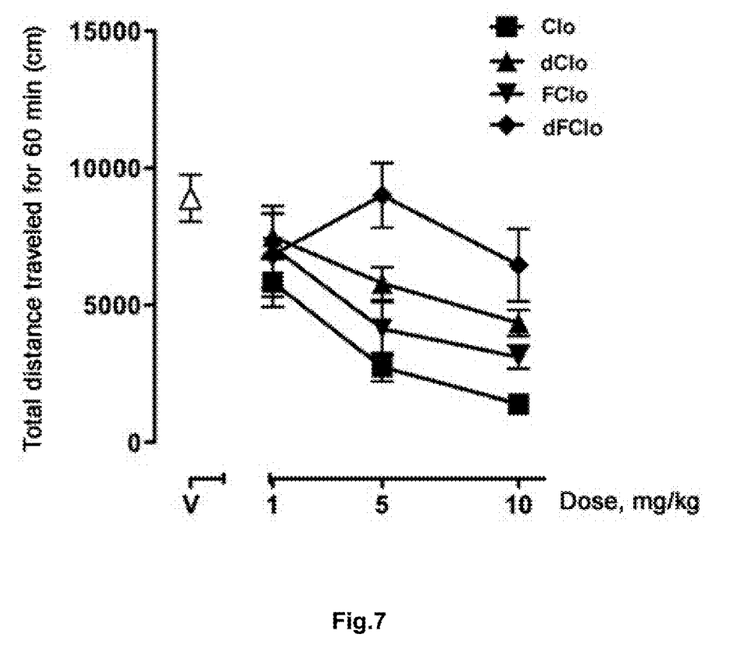
FIG. 7. Graph of the distance travelled by mice (n=8) after administration of the different doses of clozapine (Clo), desmethylclozapine (dClo), fluoroclozapine (FClo) and desmethylfluoroclozapine (dFClo).

The results of the in vitro experiments given in Example 4 have been confirmed by the studies of sedation. Halogen derivatives of clozapine as well as comparator drugs such as clozapine and desmethylclozapine were administered to CF-1 mice orally at doses of 1, 5 and 10 mg/kg (8 animals in each group). The total distance travelled by animals significantly reduced with the administration of clozapine (FIG. 7), which indicated the negative impact of sedation caused by the drug. Sedation in case of administration of halogen derivatives of clozapine was significantly lower. Desmethylfluoroclozapine at a dose of 10 mg/kg caused an insignificant decrease in motion activity.

Experimental data confirm that halogen derivatives of clozapine according to the invention have a significantly lower sedative effect than their closest structural analogues. This in turn confirms the possibility of using higher amounts of halogen derivatives of clozapine as active ingredients of pharmaceutical compositions, which makes it possible to achieve a higher therapeutic effect, since it is dose-dependent.

Example 8

Reducing the Risk of Agranulocytosis

According to modern concepts, the main cause of agranulocytosis is the formation of toxic metabolites of the compounds under the effect of myeloperoxidase, an enzyme produced by activated neutrophils during an inflammatory response and responsible for the formation of hypochlorous acid (Guest, I. et. al., Med Hypotheses, 1999, 53, 145-51). Neither clozapine (I) nor its main stable metabolites, clozapine N-oxide (VIII) and N-desmethylclozapine (VII), are not toxic in fact (Williams, D. P. et. al., J Pharmacol Exp Ther, 1997, 283, 1375-82). However, oxidation of clozapine under the effect of myeloperoxidase and hydrogen peroxide leads to the formation of clozapine nitrenium (IX), an extremely reactive compound, the toxicity of which is caused by the ability to irreversibly bind to macromolecules of cell (Liu, Z. C. et. al., J Pharmacol Exp Ther, 1995, 275, 1476-83).

to rabbits leads to increase in neutrophil release from the bone marrow and decrease in the time of their circulation in the blood (Iverson, S. et. al., *Chem Res Toxicol,* 2010, 23, 1184-91). This effect is similar to neutropenia, which is manifested in many patients at the beginning of clozapine therapy, and in most cases does not progress to its severe form—agranulocytosis. Increase in the number of neutrophils has been observed in rats after administration of aminoglutethimide, which also has a high risk of agranulocytosis (Ng, W. et. al., Chem Res Toxicol, 2013, 26, 1272-81).

The neutrophil kinetics were studied within comparative tests of sub-chronic toxicity. Studies were conducted in rats upon intragastric administration of substances at a dose of 5 mg/kg. The test substances were administered daily for 28 days. Each experimental group composed of 10 animals of each sex.

Morphological analysis of blood composition parameters in animals of experimental groups showed a significant increase in the number of circulating neutrophils in the blood of rats treated with clozapine. The number of neutrophils in the peripheral blood of rats treated with halogen derivatives of clozapine, did not differ so much different from that of the control group.

At the same time, our study has unexpectedly shown that introduction of halogen atom into the 7th position of dibenzo [b,e][1,4]diazepine ring of clozapine and its derivatives by substituents of the nitrogen atom in the 4th position of the piperazine ring, prevents the formation of toxic metabolites in the human body. Most likely, a significant decrease in toxicity is due to the fact that the introduction of a halogen atom into the 7th position prevents the most probable way of oxidation of the benzodiazepine nucleus in the human body. In addition, the acceptor properties of the introduced substituent reduce the reactivity of the nitrenium ion, and consequently lead to a decrease in the toxicity of products of oxidation of compounds and their metabolites in comparison with clozapine and N-desmethylclozapine.

The positive effect of halogen introduction into the 7th position of dibenzo[b,e][1,4]diazepine ring has been observed in pre-clinical studies of sub-chronic toxicity.

Currently, neither reliable method to predict the risk of agranulocytosis taking into account the haematological toxicity in vitro nor animal model of clozapine induced agranulocytosis exist. It is known that administration of clozapine The results of the experiments are shown in the table:

|  | Control | FClo 5 mg/kg | dFClo 5 mg/kg | Clozapine 5 mg/kg |
|---|---|---|---|---|
| Hemoglobin, g/l | 156.0 ± 2.5 | 155.4 ± 2.1 | 153.4 ± 2.4 | 154.6 ± 1.9 |
| RBC count $10^{12}$/l | 8.39 ± 0.06 | 8.43 ± 0.07 | 8.35 ± 0.07 | 8.39 ± 0.06 |
| Ht, % | 43.3 ± 0.7 | 43.2 ± 0.7 | 42.5 ± 0.5 | 43.3 ± 0.5 |
| MCV, fl | 51.6 ± 0.5 | 51.3 ± 0.5 | 50.9 ± 0.2 | 51.6 ± 0.2 |
| MCH, pg | 18.6 ± 0.2 | 18.4 ± 0.1 | 18.4 ± 0.1 | 18.4 ± 0.1 |
| MCHC, g/l | 360.2 ± 4.0 | 359.4 ± 1.9 | 360.8 ± 2.2 | 357.4 ± 1.9 |
| Rt, $10^9$/l | 81.6 ± 3.6 | 77.6 ± 4.6 | 75.6 ± 3.1 | 80.8 ± 4.1 |
| ESR, mm/h | 3.0 ± 0.3 | 4.2 ± 0.4 | 4.2 ± 0.4 | 3.8 ± 0.4 |
| PLT count, $10^9$/l | 682.6 ± 28.5 | 666.4 ± 26.0 | 653.4 ± 29.8 | 617.6 ± 43.2 |
| WBC count, $10^9$/l | 11.5 ± 1.2 | 11.2 ± 0.8 | 11.7 ± 0.9 | 11.6 ± 1.1 |
| Myelocytes, % | 0.0 ± 0.0 | 0.0 ± 0.0 | 0.0 ± 0.0 | 0.0 ± 0.0 |
| Metamyelocytes, % | 0.0 ± 0.0 | 0.0 ± 0.0 | 0.0 ± 0.0 | 0.0 ± 0.0 |
| Stab neutrophils, % | 2.4 ± 0.5 | 3.2 ± 0.4 | 4.2 ± 0.4 | 4.6 ± 0.7* |
| Segmented neutrophils, % | 20.4 ± 2.1 | 20.8 ± 1.5 | 21.4 ± 1.7 | 21.2 ± 2.0 |
| Basophils, % | 0.8 ± 0.4 | 1.0 ± 0.3 | 0.6 ± 0.3 | 0.6 ± 0.3 |
| Eosinophils, % | 0.8 ± 0.4 | 0.8 ± 0.4 | 1.0 ± 0.5 | 1.0 ± 0.5 |
| Monocytes, % | 6.6 ± 0.9 | 6.4 ± 0.5 | 6.2 ± 1.0 | 6.4 ± 0.9 |
| Lymphocytes, % | 69.0 ± 3.0 | 67.8 ± 2.4 | 66.6 ± 2.8 | 66.6 ± 2.8 |
| Plasma cells, % | 0.0 ± 0.0 | 0.0 ± 0.0 | 0.0 ± 0.0 | 0.0 ± 0.0 |

Thus, the introduction of halogen into the 7th position of dibenzo[b,e][1,4]diazepine ring reduces the risk of agranulocytosis, which indicates a significantly higher safety of the active ingredients of the pharmaceutical compositions of the invention as compared to their known structural analogues.

Example 9

Activity of Pharmaceutical Compositions in the Model of Bipolar Disorder

The ability of drugs to inhibit amphetamine-induced locomotor activity (amphetamine-induced locomotion inhibition, ALI) is a consequence of their blocking effect on dopamine receptors. Amphetamine causes a disruption of the reuptake of monoamine neurotransmitters and their accumulation in the intersynaptic space; blockade of dopamine receptors by antagonists neutralizes the excessive stimulation of dopamine signaling pathways. ALI is the basic test based on the dopamine model of bipolar disorder, and allows to evaluate the ability of drug candidates to bind to brain dopamine receptors in vivo.

During the experiment, halogen derivatives of clozapine according to the invention, clozapine and desmethylclozapine were administered to mice at doses of 1, 5 and 10 mg/kg, and spontaneous activity was recorded for an hour. After that, 3 mg/kg of d-amphetamine were administered intraperitoneally to the animals and the record of the activity was resumed. The distance (in cm) travelled by the animal in the first 60 minutes after administration of antipsychotic drugs and the distance travelled in the next hour after d-amphetamine administration were estimated.

Figure 8:
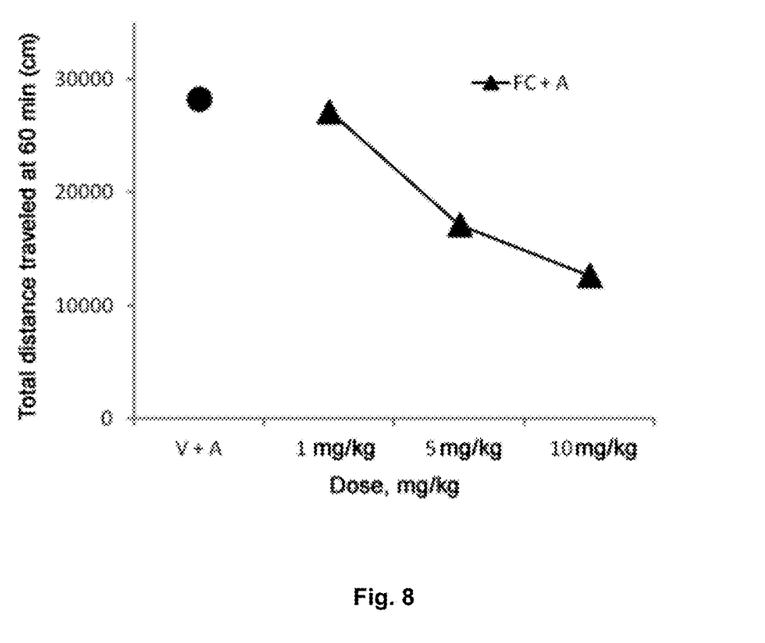
FIG. 8. Graph of the distance travelled by mice after intake of amphetamine (A) and various doses of fluoroclozapine (FC).

The results of the ALI experiments are shown in FIG. 8. In all experiments, the studied pharmaceutical compositions performed statistically significant blocking of amphetamine-induced hyperactivity, which confirms their effectiveness for the treatment of bipolar disorder. The daily therapeutic dose of fluoroclozapine designed for patient is 70 mg (1 mg/kg) according to the experiment results. The minimum effective dose designed for patient is 0.5 mg/kg, which is 20-35 mg per day, depending on patient's body weight. Taking into account the peculiarities of human metabolism, the planned initial dose of fluoroclozapine, which will cause the antidopaminergic and antiserotoninergic effect of the drug, may be 10 mg.

Example 10

Activity of Pharmaceutical Compositions in the Model of Schizophrenia

Antipsychotic effect of halogen derivatives of clozapine was studied in experiments on prepulse inhibition of acoustic startle response. Prepulse inhibition (PPI) is inhibition of motor reaction to a strong startling stimulus, usually acoustic, in the presence of a weak prestimulus. Prepulse inhibition is an indicator of sensorimotor filtering, reflecting the ability of the CNS to filter out the sensory information. Reduction in prepulse inhibition is observed in case of schizophrenia and can be simulated by intake of dopamine receptor agonists (apomorphine) or intake of NDMA antagonists (ketamine). The study of prepulse inhibition of acoustic startle response is a common test to determine the antipsychotic activity.

Antipsychotic properties of halogen derivatives of clozapine have been studied in the prepulse inhibition experiments on mice. On the day of the test animals received the test substance (fluoroclozapine at doses of 5 and 10 mg/kg) and after 25 minutes, ketamine was administered intraperitoneally at a dose of 50 mg/kg. In 5 minutes after administration of ketamine animals were placed in chambers to determine the acoustic startle response. After adaptation during 5 minutes with white background noise of 65 dB, the mice were exposed to a set of six acoustic pulses of 120 dB during 40 ms with a mean interval of 15 seconds between pulses (interval from 7 to 23 seconds) in order to estimate the intensity of initial startle reflex.

In the next set of tests, the mice were randomly exposed to one of three effects:
 a. prepulse with a duration of 20 ms and intensity of 4, 8, 12 and 15 dB, exceeding the background noise (i.e., 69 dB, 71 dB, 77 dB, 81 dB), then, after 100 ms, noise pulse with intensity of 120 dB;
 b. noise pulse with an intensity of 120 dB without any prepulse;
 c. background noise without additional pulses.

Mice were exposed to each of the effects 10 times. In the final set of tests mice were exposed to a set of six acoustic pulses of 120 dB during 40 ms.

Figure 9:
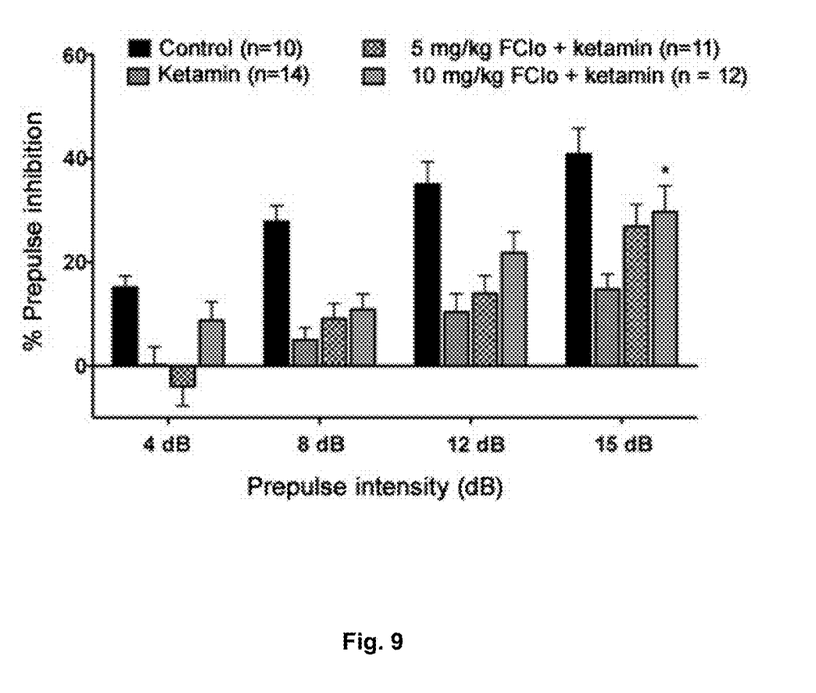
FIG. 9. Effect of fluoroclosapine on the prepulse inhibition caused by the intake of ketamine. Dependence of inhibition percentage on the prepulse inhibition intensity (in decibels) for different doses of the drugs under test, positive control (Control) and negative control (Ketamine).

The difference between the response to the first and last series of 6 acoustic pulses indicates habituation to the exposure. Such habituation is a form of non-associative learning in which the response reduction is observed after a prolonged exposure. The intensity of the prepulse inhibition is calculated as follows:

$$\% \; PPI = 100\% * \frac{[(ASRb) - (ASRa)]}{(ASRb)},$$

where ASRa is the total amplitude of acoustic startle reflex (ASR) after the a exposure (prepulse and the main noise pulse), ASRb is the amplitude of acoustic startle reflex after the b exposure (noise pulse without any prepulse).

The results of the PPI experiments are shown in FIG. 9. According to the results of experiments, halogen derivatives of clozapine demonstrated a statistically significant dose-dependent restoration of the PPI disorder caused by ketamine at a dose of 10 mg/kg in mice, which corresponds to a therapeutic dose in humans of 70 mg per day (1 mg/kg). The calculated minimum effective dose for humans is 35 mg (0.5 mg/kg).

Example 11

Maximum Tolerated Dose of Halogen Derivatives of Clozapine

To assess the safety of halogen derivatives of clozapine, the maximum tolerated dose (MTD) for miniature pigs was determined.

The maximum dose of halogen derivatives of clozapine for testing was established experimentally by dose escalation study. Initially, the pharmaceutical composition was administered at a dose of 0.53 mg/kg for 7 days. Then, on the 8th day, the administered dose of the pharmaceutical composition was increased to 1 mg/kg. After that, the dose was increased by 0.5 mg/kg every 1st, 3rd and 5th days of the seven-day cycle until an observable intoxication was noted. The doses determined during the experiment are given in the table.

|  | MTD (females) | MTD (males) |
| --- | --- | --- |
| Fluoroclozapine | 6.0 mg/kg | 5.0 mg/kg |
| Clozapine | 4.5 mg/kg | 3.0 mg/kg |

The corresponding MTDs for a human is 270 mg per day for clozapine and 450 mg per day for fluoroclozapine. However, in multicenter clinical trials demonstrating the superiority of clozapine over the other drugs, it was shown that the average dose of clozapine was 600 mg per day (CLOZARIL® label, FDA). An additional increase in the dose is possible due to the fact that with prolonged administration of clozapine, the tolerance of the drug is improved. Since the MTD of fluoroclozapine revealed in the experiment on miniature pigs was 1.7 times higher than the corresponding dose of clozapine, it can be expected that with prolonged administration in a clinical setting it will be possible to use doses of halogen derivatives of clozapine for up to 800 mg.

Thus, experiments to determine the maximum tolerated dose of drugs once again confirmed the possibility of using higher amounts of halogen derivatives clozapine as active ingredients of pharmaceutical compositions. This in turn allows to achieve a higher therapeutic effect, since it is dose-dependent.

Example 12

Pharmaceutical Compositions

The following compositions illustrate the possible, but non-limiting examples of drugs containing halogen derivatives of clozapine.

| Pill 1 | |
| --- | --- |
| Fluoroclozapine | 100 mg |
| Corn starch | 60.4 mg |
| Lactose monohydrate | 190.0 mg |
| Kollidon 30 | 17.1 mg |
| Aerosil A-300 | 3.8 mg |
| Magnesium stearate | 1.1 mg |
| Talc | 7.6 mg |

| Pill 2 | |
| --- | --- |
| Desmethylfluoroclozapine citrate | 300 mg |
| Corn starch | 181.2 mg |
| Lactose monohydrate | 380.0 mg |
| Kollidon 30 | 51.3 mg |
| Aerosil A-300 | 11.4 mg |
| Magnesium stearate | 3.3 mg |
| Talc | 15.2 mg |

| Gelcap 1 | |
| --- | --- |
| Fluoroclozapine | 100 mg |
| Corn starch | 120.2 mg |
| Povidone | 9.4 mg |
| Magnesium stearate | 50 mg |
| Talc | 8 mg |

Typically, the medication is administered to patient in need of treatment at a daily dosage. The amount of compound, which will be effective in the treatment or prevention of a particular disorder or condition, will depend, in particular, on a number of well-known factors that influence the effective dosage of medications. Dose-ranging may be individual, starting with the prescription of small doses (0.5 mg/kg) with gradual dose escalation until achieving a therapeutic effect.

Pharmaceutical compositions developed in this invention may be administered once or multiple times at intervals, for example, 1 to 3 times per day. It shall be understood that the exact dosage, regimen and duration of treatment may vary depending on age, weight and condition of a patient being treated, and may be determined empirically using any of known test protocols or through the extrapolation of the data of in vivo or in vitro tests, or of the diagnostic data. It shall be further understood that any specific dosage regimens for any particular individual shall be adjusted over time according to the individual need and professional opinion of a specialist, administering or responsible for the administration of medications.

In addition, it shall be understood that the specific dose level and frequency of administration for any particular patient may vary and depend on factors, including activity of the specific compound applied, age, body weight, general health condition, sex, diet, route of administration, drug combination, and severity of a particular condition.

Despite the fact that the invention has been described with reference to the disclosed embodiments, it should be obvious to a person skilled in the art that the specific detailed experiments are described only for illustrating the present invention and they should not be construed as in any way limiting the scope of the invention. It should be clear that it is possible to implement various modifications without departing from the essence of this invention.

The invention claimed is:

1. A method of treatment of a condition requiring selective inhibition of D4 and 5HT2A receptors, comprising administering to a patient a pharmaceutical composition containing a compound that is 11-(4-methylpiperazine-1-yl)-7-fluoro-8-chloro-5Hdibenzo[b,e][1,4]diazepine of formula (I):

in an amount effective as a selective antagonist of D4 and 5HT2A receptors, and at least one pharmaceutically acceptable carrier;

wherein the condition requiring selective inhibition of D4 and 5HT2A receptors is impulsivity or pathological gambling disorder.

2. The method of treatment according to claim 1, wherein the effective amount of the formula I compound ranges from 10 mg to 800 mg per day.

3. The method of treatment according to claim 1, wherein the effective amount of the formula I compound ranges from 50 mg to 600 mg per day.

4. The method of treatment according to claim 1, wherein the effective amount of the formula I compound ranges from 70 mg to 200 mg per day.

5. The method of treatment according to claim 1, wherein the effective amount is administered to a patient once a day.

6. The method of treatment according to claim 1, wherein the effective amount is administered to a patient twice a day.

7. The method of treatment according to claim 1, wherein administration is from two weeks up to 10 years.

8. The method of treatment according to claim 1, wherein the administration is carried out orally, intramuscularly, intravenously, or transdermally.

* * * * *